United States Patent
Weber et al.

(10) Patent No.: US 9,956,331 B2
(45) Date of Patent: May 1, 2018

(54) DEVICE AND METHOD FOR EXPRESSING HUMAN BREAST MILK

(75) Inventors: Beda Weber, Sins (CH); Etienne Furrer, Zug (CH); André Schlienger, Maschwanden (CH); Brian H. Silver, Cary, IL (US); Daniela Wäckerlin, Baar (CH); Armin Felber, Lucerne (CH)

(73) Assignee: MEDELA HOLDING AG, Baar (CH)

( * ) Notice: Subject to any disclaimer, the term of this patent is extended or adjusted under 35 U.S.C. 154(b) by 8 days.

(21) Appl. No.: 13/497,347

(22) PCT Filed: Sep. 17, 2010

(86) PCT No.: PCT/CH2010/000225
§ 371 (c)(1),
(2), (4) Date: Mar. 21, 2012

(87) PCT Pub. No.: WO2011/035447
PCT Pub. Date: Mar. 31, 2011

(65) Prior Publication Data
US 2012/0277728 A1    Nov. 1, 2012

Related U.S. Application Data

(60) Provisional application No. 61/244,636, filed on Sep. 22, 2009.

(51) Int. Cl.
*A61M 1/06* (2006.01)
*A61M 1/00* (2006.01)

(52) U.S. Cl.
CPC ............ *A61M 1/06* (2013.01); *A61M 1/0072* (2014.02); *A61M 1/064* (2014.02); *A61M 1/066* (2014.02)

(58) Field of Classification Search
CPC .............. A61M 1/06; A61M 2001/062; A61M 2001/064; A61M 1/064; A61M 1/0072
(Continued)

(56) References Cited

U.S. PATENT DOCUMENTS

| 949,414 A | 2/1910 | Cunningham |
| 4,799,922 A | 1/1989 | Beer et al. |

(Continued)

FOREIGN PATENT DOCUMENTS

| EP | 1219833 | 7/2002 |
| EP | 2127690 | 12/2009 |

(Continued)

OTHER PUBLICATIONS

English Translation of the Int. Preliminary Report on Patetablity for Int. App. No. PCT/CH2010/000225, dated Apr. 12, 2012.

(Continued)

*Primary Examiner* — Theodore Stigell
*Assistant Examiner* — Benjamin Koo
(74) *Attorney, Agent, or Firm* — McDonnell Boehnen Hulbert & Berghoff LLP

(57) ABSTRACT

A device for expressing human breast milk has a breast shield for bearing against a mother's breast, a vacuum pump for generating a vacuum, a line which connects the vacuum pump to the breast shield and is intended for transmitting the vacuum generated to the breast shield, and a chamber. The line ends on the pump side in a first port of the chamber. The chamber has a second port for connection to a milk collecting container. The two ports in the chamber are connected to each other in terms of fluid communication. During the expressing operation, the line forms a milk line for transporting breast milk expressed in the breast shield to the chamber and from the chamber to the milk collecting container. The pump can be designed to be quiet and small.

9 Claims, 7 Drawing Sheets

(58) Field of Classification Search
USPC .................................................. 604/73–74
See application file for complete search history.

(56) References Cited

U.S. PATENT DOCUMENTS

| | | | |
|---|---|---|---|
| 4,857,051 A | 8/1989 | Larsson | |
| 4,929,229 A | 5/1990 | Larsson | |
| 5,601,531 A | 2/1997 | Silver | |
| 5,616,125 A * | 4/1997 | Jelks | 604/74 |
| 6,161,710 A | 12/2000 | Dieringer et al. | |
| 6,379,327 B2 | 4/2002 | Lundy | |
| 6,440,100 B1 | 8/2002 | Prentiss | |
| 6,461,324 B1 | 10/2002 | Schlensog | |
| 6,663,587 B2 | 12/2003 | Silver et al. | |
| 6,669,064 B2 | 12/2003 | Perricone | |
| 7,070,400 B2 | 7/2006 | Greter | |
| 7,094,217 B2 | 8/2006 | Fialkoff | |
| 7,223,255 B2 | 5/2007 | Myers et al. | |
| 7,238,165 B2 * | 7/2007 | Vincent | A61M 1/1053 417/412 |
| 7,559,915 B2 | 7/2009 | Dao et al. | |
| 7,662,127 B2 | 2/2010 | Silver et al. | |
| 7,833,190 B1 * | 11/2010 | Hall | 604/74 |
| 2004/0071572 A1 | 4/2004 | Greter | |
| 2004/0087898 A1 * | 5/2004 | Weniger | 604/74 |
| 2005/0043677 A1 | 2/2005 | Kelly et al. | |
| 2005/0154349 A1 | 7/2005 | Renz et al. | |
| 2005/0222536 A1 * | 10/2005 | Silver | 604/74 |
| 2006/0106334 A1 | 5/2006 | Jordan et al. | |
| 2007/0078383 A1 | 4/2007 | Tashiro et al. | |
| 2008/0039781 A1 | 2/2008 | Bjorge | |
| 2008/0090445 A1 | 4/2008 | Luzbetak et al. | |
| 2008/0146118 A1 | 6/2008 | Solberg et al. | |
| 2008/0171970 A1 | 7/2008 | Luzbetak et al. | |
| 2008/0243059 A1 | 10/2008 | Yamashita et al. | |
| 2008/0255503 A1 | 10/2008 | Quackenbush et al. | |
| 2008/0287037 A1 | 11/2008 | Solberg | |
| 2009/0062731 A1 | 3/2009 | Keyong et al. | |
| 2009/0099511 A1 | 4/2009 | Sutrina et al. | |
| 2009/0264837 A1 * | 10/2009 | Adahan | 604/290 |

FOREIGN PATENT DOCUMENTS

| | | |
|---|---|---|
| JP | 2004-522890 | 7/2004 |
| JP | 2008-538955 | 11/2008 |
| KR | 2004-0051728 | 6/2004 |
| SU | 1319 | 9/1924 |
| WO | 96/22116 | 7/1996 |
| WO | 99/44650 | 9/1999 |
| WO | 02/102437 | 12/2002 |
| WO | 2005/067997 | 7/2005 |
| WO | 2006/117352 | 11/2006 |
| WO | 2008/008781 | 1/2008 |
| WO | 2008/057218 | 5/2008 |
| WO | 2008/090386 | 7/2008 |
| WO | 2008/137678 | 11/2008 |

OTHER PUBLICATIONS

English Translation of the Int. Preliminary Report on Patetablity for Int. App. No. PCT/CH2010/000226, dated Apr. 12, 2012.
International Search Report for Int. App. No. PCT/US2010/049355 dated May 16, 2011.
International Search Report for International Patent App. No. PCT/CH2010/000226, dated Jan. 4, 2011.
International Search Report for International Patent App. No. PCT/CH2010/000225, dated Jan. 12, 2011.

* cited by examiner

US 9,956,331 B2

DEVICE AND METHOD FOR EXPRESSING HUMAN BREAST MILK

CROSS REFERENCE TO RELATED APPLICATIONS

The present application is a U.S. National Phase Application pursuant to 35 U.S.C. § 371 of International Application No. PCT/CH2010/000225 filed Sep. 17, 2010, which claims priority to U.S. Provisional Patent Application No. 61/244,636 filed on Sep. 22, 2009. The entire disclosure contents of these applications are herewith incorporated by reference into the present application.

TECHNICAL FIELD

The present invention relates to a device for expressing human breast milk, a vacuum pump and to a method for operating a device for expressing human breast milk.

BACKGROUND

Devices for expressing human breast milk are well known. In principle, there are two different types: the first device type is operated manually, i.e. the negative pressure required for the expressing operation is generated by manual actuation of the vacuum pump. In the devices of the second type, the vacuum pump is operated electrically, it being possible for the vacuum pump to be connected to the power supply network and/or to be operated via a battery or another energy accumulator. Examples for this include WO 96/22116, US 2009/0099511, US 2008/0287037, U.S. Pat. No. 7,094,217 and US 2008/0039781.

The vacuum pumps are connected to a breast shield either directly or via vacuum lines. The breast shield usually has a funnel-shaped part for receiving part of the mother's breast including the nipple. As a rule, the funnel-shaped part merges into a part, which is in the shape of a hollow cylinder and to which, firstly, either the vacuum pump is connected directly or via a suction line and which, secondly, is likewise connected directly or via a milk line to a milk collecting container. It is known to select breast shields in accordance with the size of the breast. In particular, breast shield sets are known, in which the size of the funnel-shaped part can be selected according to the mother.

Relatively small breast shields are also known in the prior art. U.S. Pat. No. 6,379,327 discloses a portable, so called "hands-free" expressing device. In this context, "hands-free" means that, once switched on, the entire expressing device functions without hands, i.e. that neither the pump nor the breast shield have to be held by hand. In U.S. Pat. No. '327, a small funnel-shaped breast shield is fastened for this purpose to the breast using straps. A first tube leads from the breast shield to a vacuum pump, which is held in a belt. A second tube leads from the breast shield into a milk collecting container, which can be carried in the same belt.

WO 02/102437 and WO 2008/137678 show "hands-free" expressing devices as well. Here, the breast shield is in each case integrated into a pump housing and serves at the same time as a diaphragm for generating a negative pressure.

U.S. Pat. No. 949,414 describes a funnel-shaped breast shield, which can be arranged under a bra. Rather than a vacuum being applied, a tube leads from the breast shield to a baby who is intended to obtain the milk desired by sucking on the tube.

U.S. Pat. No. 6,440,100 shows a device for expressing breast milk with a small breast shield, which can be worn under the bra. A milk tube leads from the breast shield to a milk collecting container. The container is connected via a vacuum tube to a vacuum source. The milk collecting container is evacuated by means of the vacuum source, with the negative pressure being applied to the breast shield via the milk tube. Because of the negative pressure prevailing in the milk collecting container, expressed milk is to pass into the milk collecting container via the milk tube. As an alternative, the milk collecting container itself can serve as a vacuum pump. The device has the disadvantage that the relatively large volume of the milk collecting container likewise has to be evacuated. The "dead volume" considerably restricts the performance of the device.

SUMMARY OF THE INVENTION

It is an object of the invention to provide an improved device and an improved method for expressing human breast milk.

The device according to the invention for expressing human breast milk has a breast shield for bearing against a mother's breast, a vacuum pump for generating a vacuum, a line that connects the breast shield to the pump chamber and is intended for transmitting the vacuum generated to the breast shield, and a chamber. The line ends on the pump side in a first port of the chamber. According to the invention, the chamber has a second port for connection to a milk collecting container. The two ports in the chamber are connected to each other in terms of fluid communication. During the expressing operation, the line forms a milk line for transporting breast milk expressed in the breast shield to the chamber. The milk is subsequently conducted from the chamber to the milk collecting container.

In the method according to the invention for operating a device for expressing human breast milk, a vacuum is generated in a breast shield by means of a vacuum pump, the vacuum generated being conducted from a chamber via a line to the breast shield, and expressed milk being collected via the breast shield in a milk collecting container. According to the invention, during the expressing operation, the same line, which is used for transmitting the vacuum, conducts the milk expressed in the breast shield to the chamber, and, during the expressing operation, the milk being conducted further from the chamber into a milk collecting container.

The device therefore changes from an initial pneumatic pumping system to a hydraulic pumping system, wherein the same line is used. In this case, the expressed milk acts as working fluid in order to express further milk from the breast. Furthermore, the milk that has already been expressed heats the breast shield, which is pleasant for the mother.

The device according to the invention and the method according to the invention require only a single tube connection, even if the milk collecting container is not arranged directly on the breast shield. The device can therefore also be configured and used as a "hands-free" device. The breast shield can be designed to be small and can be fixed in a bra. The single line can be discretely concealed in the clothing.

Since the entire system is flooded by milk and there is therefore no longer a vacuum line in the classic sense, a lower pumping power is required in order to express breast milk. Typical values for air output are up to 500 ml/min and for milk output up to 100 ml/min. The vacuum pump can therefore be configured to be smaller and lighter, so as to be less conspicuous to onlookers. The mother can use the vacuum pump more discreetly. In addition, due to the lower pumping power requirement, the vacuum pump is quieter during use, which in turn increases the comfort and discretion.

Since the entire system apart from the pumping-unit-side or drive-side region of the vacuum pump, is flooded with milk and there are only very small air-filled dead spaces, if any at all, the applied vacuum can more easily be controlled. The negative pressure present at the breast shield also corresponds more to the vacuum generated in the vacuum pump.

The milk line can be realized in various ways. In a preferred embodiment, there is a partition wall, which separates a vacuum pump drive and the line from each other. As a result, the chamber is divided by the partition wall into a breast-shield-side region and a drive-side region. The two regions are completely separated from each other and are connected to each other only via the diaphragm. Thus, milk does not pass into the drive-side region of the vacuum pump, nor does dirt or air pass from the drive-side region pass into the milk-conducting line and therefore into the breast shield and the milk collecting container. The partition wall is preferably a diaphragm.

In a preferred embodiment, the diaphragm is driven and serves to convey the expressed milk. As a result, the milk can be expressed independently of the relative position of the breast shield, the milk collecting container, and the vacuum pump with respect to one another. The mother may, for example, even express milk while lying down. This is optimum in particular in a "hands-free" embodiment since the mother may bend down and in general move very freely.

A very wide variety of vacuum pumps can be used with the vacuum-transmitting and milk-conducting line according to the invention. Preferably, but not necessarily, a single diaphragm is used in each case both for transporting the milk and for separation of the media.

The vacuum pump is preferably a diaphragm pump, wherein the chamber is the vacuum-generating pump chamber of the vacuum pump, and the diaphragm is the diaphragm of the pump chamber used for generating the vacuum.

A preferred vacuum pump according to the invention for expressing human breast milk by means of a breast shield has a drive and a diaphragm that can be driven cyclically by the drive, the diaphragm being arranged in a chamber, the diaphragm separating the chamber into a drive-side part and a breast-shield-side part, and the breast-shield-side part having a vacuum port for producing a connection to the breast shield. According to the invention, the breast-shield-side part of the chamber furthermore has a milk port for producing a connection to a milk collecting container, and the vacuum port and the milk port are connected to each other in terms of fluid communication via the breast-shield-side part of the chamber. Preferably, the vacuum pump is a diaphragm pump and the chamber is the vacuum-generating pump chamber.

The vacuum pump may have, but does not have to have, the abovementioned vacuum-transmitting and milk-conducting line. In another embodiment, the vacuum pump for the breast shield is connected directly to the first port of the chamber.

In a preferred embodiment, the vacuum pump is an electric diaphragm pump. In this case, the diaphragm of the diaphragm pump preferably forms the abovementioned diaphragm serving as a drive for the milk and as a partition wall. The drive of the diaphragm preferably serves simultaneously to generate the vacuum in the pump chamber and to convey the flow of milk. Due to the triple function of the diaphragm, the vacuum can be better controlled.

The diaphragm preferably has a substantially circular outline. The diaphragm is preferably driven in the central region thereof, preferably in the center thereof.

Other types of diaphragm pumps having, for example, a flat coil or a moving coil as the drive system can also be used. Alternative pumps without a diaphragm may also be used. Furthermore, manually driven pumps may be used.

There is preferably a nonreturn valve or another one-way valve, which creates a connection between the chamber and the milk collecting container. As a result, the connection to the milk collecting container is opened only when the remaining system has already been filled as completely as possible with milk or when there is a sufficiently large pressure in the chamber. Heavy loading of the vacuum pump by possible air-filled dead volumes is again also avoided here. The second port and therefore also the valve are arranged at the bottom in the correct position of operation of the vacuum pump. The valve is located in the breast-shield-side region of the chamber, which region is also referred to as the line-side region. By contrast, the first port is preferably arranged in the upper region of the chamber. As a result, air from the chamber is conducted into the milk collecting container and air-filled dead volumes and air bubbles in the system are avoided.

The device according to the invention and the method according to the invention can be used with all types of breast shields. Preferably, however, small breast shields are used in order to keep the dead volume as small as possible.

Preferably, a breast shield is used, which only surrounds the nipple, and at maximum may also surround the aerola. Not only can the breast shield be used in a simple manner in a "hands-free" system, for example can be kept in a bra, the breast shield also has scarcely any air-filled regions because of its small size. This has a positive effect on the vacuum pump since the pump requires less power and can therefore operate more quietly. Furthermore, for this reason, the vacuum pump can also be made smaller.

In addition, breast shields of this type have the advantage that there can be less movement of the tissue of the breast within the shield. As a result, the breast shields can bear more tightly against the tissue. A lower pumping power is required as a result. The pump again can be designed to be smaller and operate more quietly.

According to the invention, the device has a breast shield which adapts itself optimally to the shape of the human mother's breast therefore creates a tight or less tight connection to the breast, depending on requirements.

Such a breast shield according to the invention has a tubular connector and a funnel that is integrally formed thereon and is intended for resting on a mother's breast, wherein the funnel widens toward the free side thereof that faces away from the connector, and wherein there is a passage, which extends continuously from a breast-side end of the funnel as far as a pump-side end, being opposite said breast-side end, of the connector and which serves to apply a vacuum to the mother's breast and for the flowing away of the expressed breast milk. According to the invention, the funnel is of more flexible design than the connector, and the funnel has a main region extending over a substantial part of the length thereof with a first opening angle of the passage, and a breast-side end region with a second opening angle of the passage. When not in use, the first opening angle is smaller than the second opening angle. In use, at least the first opening angle can be enlarged by axial pressure on the breast shield.

The breast shield can also be used in other devices for expressing breast milk and is not restricted to the use of lines which simultaneously transmit a vacuum and conduct milk or to the use of the above-described chambers.

In contrast to the known breast shields and to the natural sucking of a baby, the nipple in a breast shield of this type is customarily not expanded to 2.5 times the length thereof. This is pleasant for the mother, in particular if she has painful nipples.

When not in use, typical values of the first opening angle of the breast shield are ≤5° (smaller or equal to 5°) and of the second opening angle are 90° to 160°. During use and depending on the axial pressure applied, at least the second opening angle can be enlarged up to 120°, preferably up to 160°.

The funnel preferably has a breast-side diameter of 5 mm to 40 mm and a length of 10 mm to 40 mm, and therefore, in use, the nipple, and at maximum the areola, is surrounded by the breast shield. Milk ducts in the breast tissue are preferably not surrounded by the breast shield.

Between the connector and funnel, there is preferably a transition region with a third opening angle of the passage, wherein the third opening angle is larger than the first opening angle when the device is not in use.

Typical values of the third opening angle are 60° to 150°.

The main region preferably directly adjoins the transition region. The end region preferably also directly adjoins the main region.

In a preferred embodiment, the connector has a wall thickness that is much greater than the wall thickness of the funnel. As an addition or alternative, the connector may also be formed from a material having a greater shore hardness.

In the transition region between the connector and funnel there is preferably an outer stop, which protrudes over the outer circumference of the connector.

The connector can be readily inserted into a recess if the outer circumference of the connector is designed such that it widens conically toward the funnel.

The breast shield according to the invention is preferably manufactured from silicone and preferably has a Shore A hardness of 30 to 70. The funnel preferably has a Shore A hardness of about 50. The connector has preferably a Shore A hardness of about 70.

So that the relatively small and compact breast shield can be readily held in the hand, a coupling part is preferably provided in a breast shield set. The coupling part serves to receive the breast shield connector in a sealing manner, wherein the coupling part is of cylindrical design and is closed on one side by a base such that a blind hole for receiving the connector is formed. There is a port opening, which is connected to the passage of the breast shield in terms of fluid communication.

In the assembled state, an end side of the connector remote from the breast shield preferably ends at a distance from the base of the coupling part. The port opening is preferably arranged eccentrically in the coupling part.

If the port opening is arranged in an upper region of the coupling part and the coupling part has a marking, which defines "this side up" in the space, then, during the expressing operation, stationary air bubbles are avoided in the coupling parts and air-filled dead spaces are eliminated.

In order to be able to insert the conical connector more easily, the blind hole of the coupling part also tapers in diameter toward the base.

The coupling part is preferably of stiff design, this facilitating the insertion of the connector and increasing the stability. The part can therefore be more easily held or fastened.

The combination of the three elements a vacuum-transmitting and milk-conducting line, a pump chamber diaphragm with its triple function, and the breast shield that is of small design and avoids dead volumes results in a device that can be designed to be small and quiet, and furthermore is optimally suitable for any type of use, in particular "hands-free" use.

Further advantageous embodiments and variants of the method are indicated in the dependent claims.

BRIEF DESCRIPTION OF THE DRAWINGS

Preferred embodiments of the invention are described below with reference to the drawings that serve merely for explanation and should not be interpreted as being limiting. In the drawings.

The same parts are provided with the same designations in the Figures.

DESCRIPTION OF PREFERRED EMBODIMENTS

Figure 1:
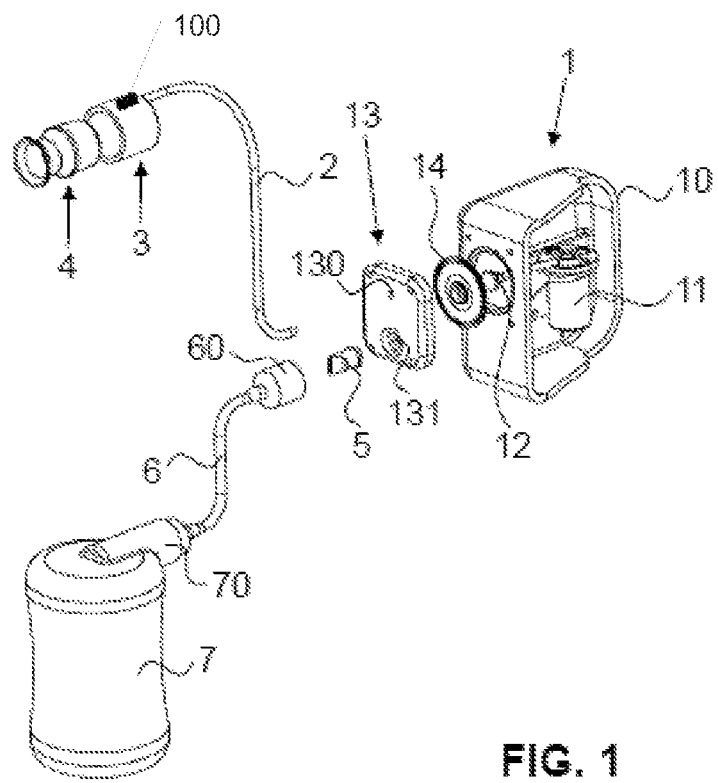
FIG. 1 shows an exploded view of a first embodiment of a device according to the invention, in which a side wall of the vacuum pump is not illustrated.
Figure 2:
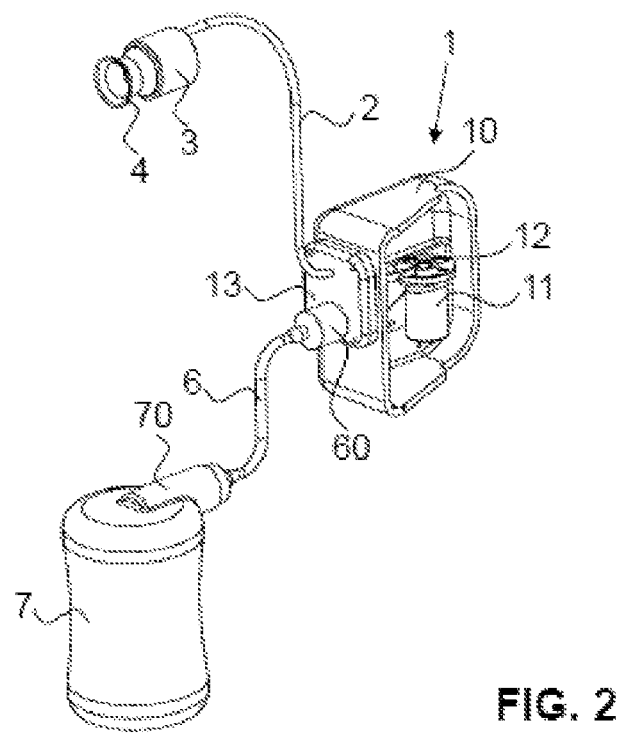
FIG. 2 shows the device according to FIG. 1 assembled for use, in which a side wall of the vacuum pump is not illustrated.
Figure 3:
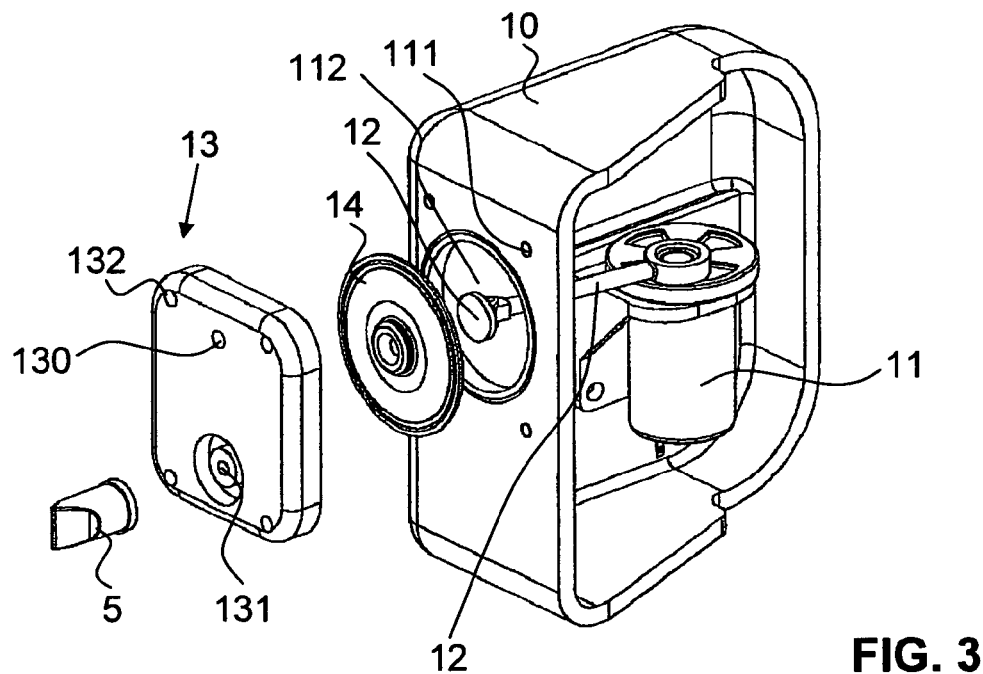
FIG. 3 shows an exploded view of the vacuum pump from a first side.
Figure 4:
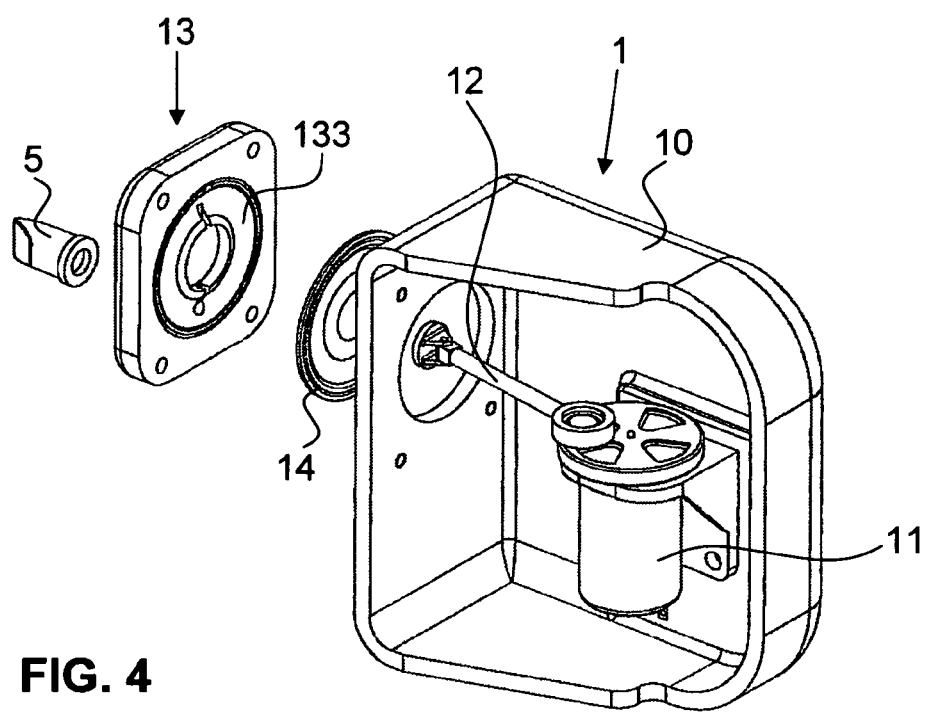
FIG. 4 shows the vacuum pump according to FIG. 3 from a second side.
Figure 5:
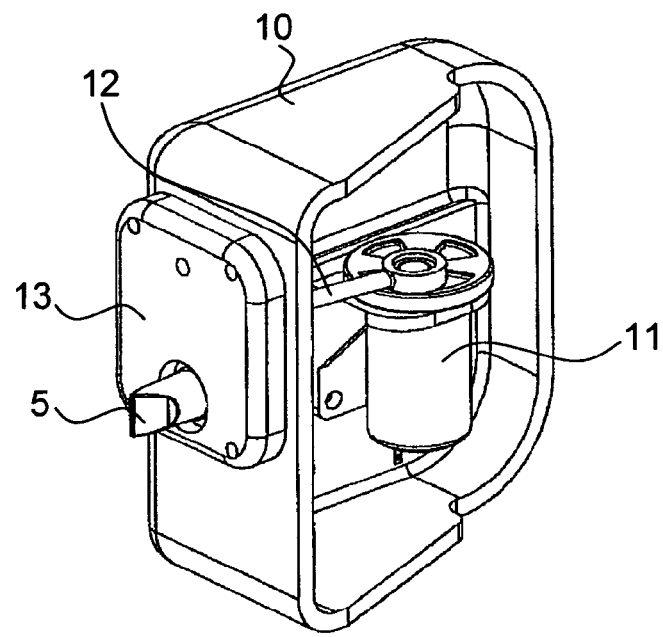
FIG. 5 shows the vacuum pump according to FIG. 3 assembled for use, but without a side wall.

FIGS. 1 to 5 illustrate a first embodiment of the device according to the invention. The device has a vacuum pump 1, a first line 2, a coupling part 3, a breast shield 4, a nonreturn valve 5, a second line 6, and a milk collecting container 7.

The breast shield 4 is connected to the vacuum pump 1 via the coupling part 3 and the first flexible line 2. The second flexible line 6 leads from the vacuum pump 1 to the milk collecting container 7, the connection being provided with the nonreturn valve 5. The two flexible lines 2, 6 are preferably tubes, preferably made of silicone.

Figure 6:
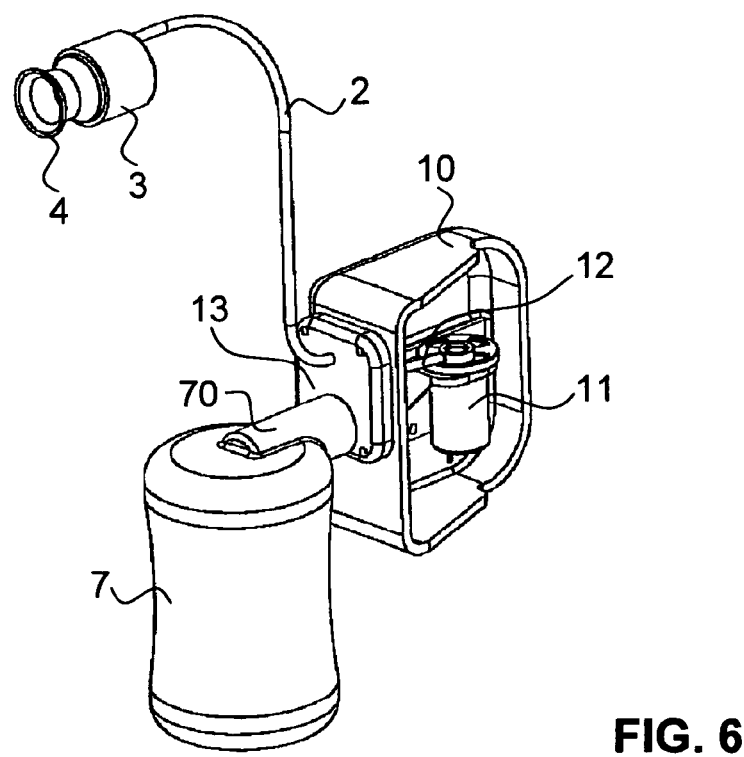
FIG. 6 shows a second embodiment of a device according to the invention, in which a side wall of the vacuum pump is not illustrated.

As illustrated in FIG. 6, the milk collecting container 7 may alternatively be fastened directly to the vacuum pump 1. For this purpose, there is preferably a suitably shaped adapter 70 on the milk collecting container 7, the adapter being detachably connectable to a housing 10 of the vacuum pump.

The vacuum pump 1 has the abovementioned housing 10, a side wall of the housing 10 not being illustrated in the drawings. As a result, the interior of the housing 10 can be revealed. This can be readily seen in FIGS. 3 to 5. There is an electric motor 11 in the housing 10. The electric motor can be operated from the electric supply network and/or the motor can be battery operated.

A force transfer unit 12, here a piston rod connected to the motor, transfers the rotational movement of the motor into a linear movement. The connecting rod 12 is connected at the second end thereof to a diaphragm 14. The diaphragm 14 is arranged in a recess 112 of the housing 10, which forms part of a pump chamber. A cover 13 that is detachably connectable to the housing 10 secures the diaphragm 14 in its position.

Instead of the drive, other types of drives, in particular even manual drives, can also be used.

The cover 13 is preferably screwed to the housing 10. Other types of connections are likewise possible. The cover 13 likewise has a recess 133 such that the cover forms a second part of the pump chamber. The two parts of the pump chamber are separated from each other by the diaphragm 14. The cover 13 can be formed as a single piece or as a number of pieces.

The principle of operation of the diaphragm pump is not described in detail here since it is well known. By means of a drive, here by means of a motor 11 and connecting rod 12, the diaphragm is moved cyclically to and fro such that a negative pressure is generated in the breast-shield-side or cover-side part of the pump chamber. Instead of the drive illustrated here, other types of drives suitable for moving the diaphragm 14 cyclically can also be used. The electronics required for operating the pump and the control elements are not illustrated here. The pump can be operated with a temporally constant cycle, or, as is known in the prior art, the suction curve may be adapted in the shape, frequency, and intensity thereof to the suction behavior of the baby and/or to the requirements of the mother.

In the cover 13, i.e. in the valve plate, there is a first outlet opening 130, which connects the environment to the cover-side part of the pump chamber. The outlet opening 130 serves as a first port for the first line 2. A second outlet opening 131, which likewise connects the cover- and breast-side part of the pump chamber to the surroundings, respectively, is designed as a second port. The second port is provided with the nonreturn valve 5. A duckbill valve may be plugged onto a connector. However, other types of valve are also usable.

In use, the breast shield 4 is placed onto the mother's breast such that the breast shield at least surrounds the nipple. Preferably, at maximum the areola is additionally surrounded by the breast shield 4. The vacuum pump 1 is switched on and operated in a known manner. The vacuum generated in the pump chamber evacuates the first line 2 such that there is a negative pressure in the breast shield 4. As a result, milk is expressed from the mother's breast and passes through the breast shield 4 and the coupling part 3 into the first line 2. The milk flows through the first outlet port 130 into the cover-side part of the pump chamber. The expressed milk leaves the pump chamber through the second outlet port 131 and the nonreturn valve 5 and passes into the milk collecting container via the second line 6 (see FIG. 2) or else, depending on the embodiment, directly (see FIG. 6). There is therefore no separate line for transporting the milk. The first line 2 serves at the same time as a suction line and as a milk transport line. After initial pneumatic pumping, the device therefore changes to hydraulic pumping. This is a further approximation to the natural sucking of babies.

The diaphragm 14 in the pump chamber has three functions. First, the diaphragm forms the diaphragm of the diaphragm vacuum pump and thus generates the vacuum in the pump chamber. Second, the diaphragm serves as a partition wall between the air in the pump-side part of the pump chamber and the milk in the cover-side part of the pump chamber. The diaphragm therefore serves as a means of separating media and prevents milk from being able to pass into the pump unit. However, the diaphragm also prevents dirt from the pump unit from being able to pass into the first and second lines 2, 6. Third, the cyclic movement of the diaphragm within the pump chamber results in said diaphragm conveying and transporting the milk. Due to the third function of the diaphragm 14, during the expressing operation, the milk collecting container 7, breast shield 4, and vacuum pump 1 can be arranged in positions which are independent of one another. For example, the milk collecting container 7 can be located above the vacuum pump 1 and/or the breast shield 4. The vacuum pump 1 may also be above the milk collecting container 7 and/or the breast shield 4. This enables the mother to express milk even while lying down or, if she is seated, to place the milk collecting container 7 and the vacuum pump 1 onto a shelf or another raised platform out of the reach of small children.

In the examples according to FIGS. 1 to 6, a negative pressure of 0 to 300 mmHg is preferably generated. The pumping frequency is preferably between 5 and 120 cycles per minute.

In one embodiment, the nonreturn valve 5 preferably opens only when there is sufficient pressure, i.e. when the pump chamber is sufficiently filled with milk. As a result, the dead volume, which has to be evacuated, can be kept to a minimum.

In addition, the dead volume can be reduced by use being made of a small breast shield 4, which only surrounds the nipple and as small a part of the remaining breast as possible, if any part of the remaining breast at all. A suitable breast shield 4 according to the invention is illustrated in the figures. The breast shield and the coupling part 3 thereof can readily be seen in FIGS. 7 to 11.

Figure 7A:
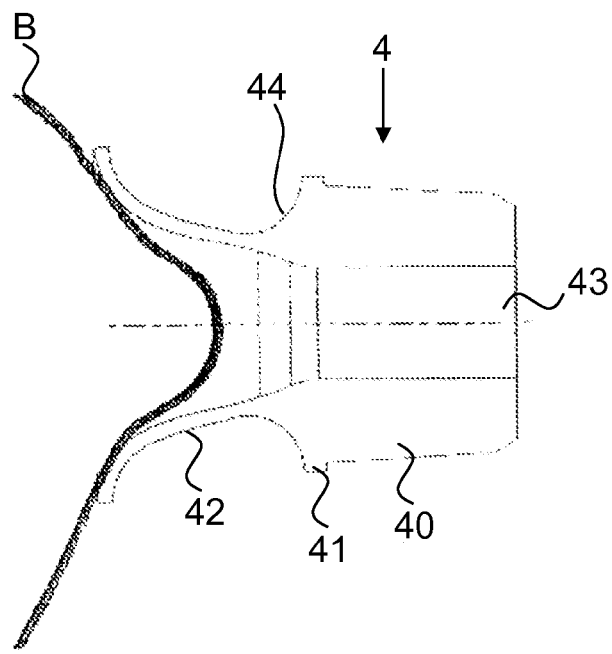
FIG. 7a shows a longitudinal section through a breast shield according to the invention, applied to a human breast with a relatively large contact pressure.

FIG. 7a shows a breast shield 4 according to the invention applied to a female breast B. The breast shield 4 has a connector 40, a funnel 42, and a transition region 44 connecting these two. There is preferably a radially outwardly protruding flange 41 between the connector 40 and funnel 42. A continuous passage 43 extends through the entire breast shield 4 such that the breast shield is designed to be open at two opposite ends. The breast shield 4 is preferably of rotationally symmetrical design.

The breast shield 4 is preferably designed as a single piece and is customarily composed of plastic, preferably of silicone, for example.

The connector 40 is of solid design, i.e. relatively stiff design, and serves for the coupling to the coupling part 3. The connector 40 has a wall thickness which is much greater than the wall thickness of the funnel 42. In this example, the connector 40 is of conical design at the outer circumference thereof while the connector is preferably of rotationally symmetrical design. The conicity facilitates the insertion into the coupling part 3 and, in addition, increases the tightness of the connection to the coupling part 3. The tightness is furthermore obtained by the connector 40, due to the material, being slightly compressed in the coupling part. For this purpose, the outside diameter of the connector 40 is slightly larger than the inside diameter of the coupling part 3. Example external diameters of the connector 40 are 8 mm to 40 mm. Example lengths are 5 mm to 40 mm.

The funnel 42 serves to receive the mother's breast. The funnel is preferably configured to be highly flexible. The funnel is of substantially more flexible and soft design than the connector 40. Due to the flexibility thereof, the funnel adapts its shape to the shape of the breast. The funnel 42 has a smaller wall thickness than the wall thickness of the connector 40. Alternatively, the connector 40 and funnel 42 may also have the same wall thickness, wherein, in this case, the connector 40 is preferably manufactured from a material having a greater Shore hardness or has reinforcement. The funnel 42 preferably has a Shore A hardness of about 50 and the connector 40 has a Shore A hardness of about 70.

Figure 7B:
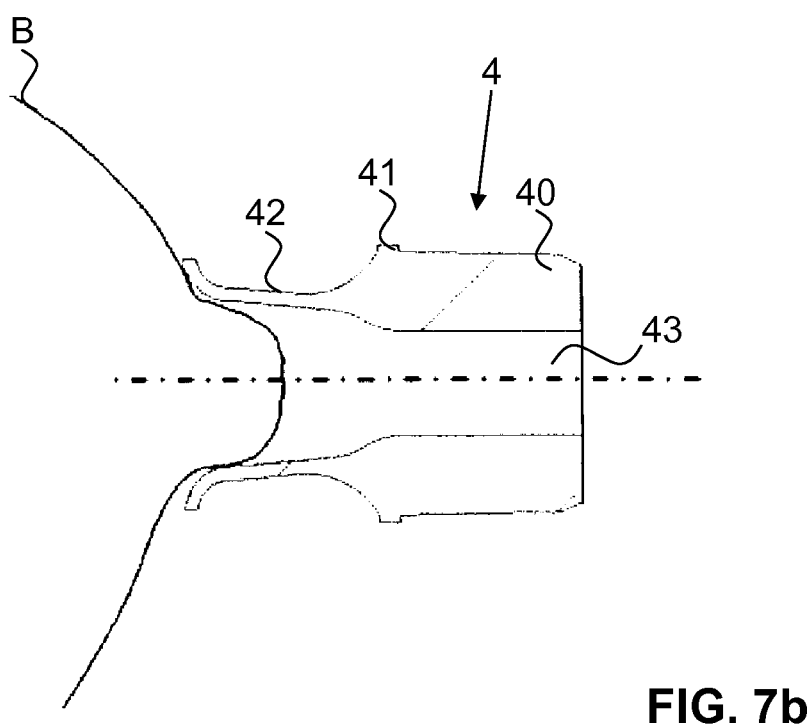
FIG. 7b shows a longitudinal section through the breast shield according to the invention according to FIG. 7a, applied to a human breast with a smaller contact pressure.
Figure 8:
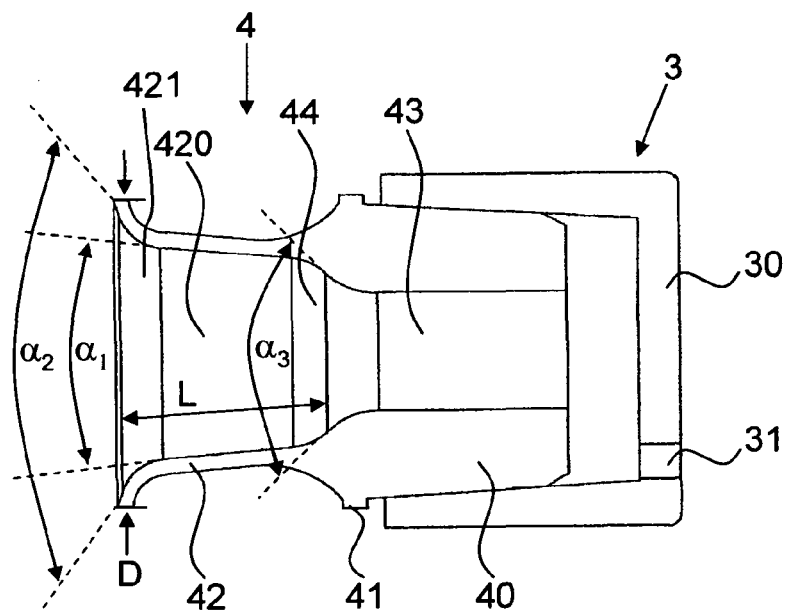
FIG. 8 shows a longitudinal section through the breast shield according to FIG. 7b with a coupling part in a first embodiment.

FIG. 8 illustrates the breast shield 4 when not in use. The funnel 42 has at least two regions: a main region 420 and a front, breast-shield-side end region 421. When not in use, the main region 420 has a first opening angle $\alpha_1$ and the end region has a second opening angle $\alpha_2$. The first opening angle $\alpha_1$ is smaller than the second opening angle $\alpha_2$. In addition, the wall is preferably bent over outward in the end region 421. As can be seen in FIGS. 7a and 7b, the first opening angle $\alpha_1$ can be enlarged upon axial contact pressure on the breast such that the end region 421 can be optimally adapted to the shape of the breast.

As can be seen in the figures, the main region 420 directly adjoins the end region 421. At the other end, the main region 420 directly adjoins the transition region 44.

In the transition region 44 there is a further, third opening angle $\alpha_3$, which is likewise larger than the first opening angle $\alpha_1$ of the main region 420. The third opening angle serves as a predetermined value for the main region for enlarging the angle.

The angles when not in use are preferably, for the first opening angle $\alpha_1 \leq 5°$, for the second opening angle $\alpha_2$, 90° to 160°, and for the third opening angle $\alpha_3$, 60° to 150°. When in use, at least the first opening angle $\alpha_1$ can be enlarged to an angle of up to 10°.

The funnel 42 has a length L of 10 mm up to 40 mm. The diameter D in the front end region is preferably 5 mm to 40 mm, preferably 20 mm to 40 mm. As a result, the funnel 42 is so small that the funnel surrounds only the nipple or in addition, at the most a portion or all of the areola of the breast. This corresponds approximately to the portion of the breast, which is taken into the mouth by a baby. The funnel 42 is of frustoconical design in the region of the connector 40, the funnel opening toward the breast. The front, breast-side border thereof is inclined outward to a greater degree than the connector-side part.

Since the breast shield 4 or at least the funnel 42 is configured to be flexible, the mother, by choosing the contact pressure, can select how much of the breast is actually surrounded by the breast shield 4. The contact pressure is produced from the axial pressure on the funnel 42 and the counterpressure from the mother's breast. In FIG. 7a, the contact pressure is relatively large and the funnel is expanded, and, in FIG. 7b, the pressure is smaller and the funnel 42 merely encloses the nipple. By choosing the contact pressure, the tightness of bearing against the breast can also be adjusted and therefore the expressing operation can be adjusted to be as comfortable as possible for the mother.

As can be seen in FIG. 8, the breast shield 4 is plugged into the coupling part 3. The coupling part 3 is preferably likewise configured to be small, but to be as stiff as possible. In the outer circumference thereof, the coupling part is preferably of cylindrical design and, in the inner circumference thereof, is frustoconical or conical, respectively. The coupling part 3 has a U-shaped cross section, i.e. is designed to be open at one end and closed at the opposite end. There is therefore a blind hole, into which the connector 40 of the breast shield 4 can be pushed as far as the stop 41. In FIG. 8, the breast shield 4 is not yet fully pushed in. As can be seen, however, in the fully-pushed in state, there is a gap between the end side of the connector 40 and the rear wall of the coupling part 3, the gap forming a fluid passageway from the passage 43 to a port opening 31 in the coupling part 3.

The port opening 31 serves for the connection of the first line 2. The first line 2 may simply be plugged into the port opening, may be connected fixedly to the coupling part 3, or there may be plug-in or plug-on means, for example connectors, for connection to the first line 2.

Figures 9, 10, 11:
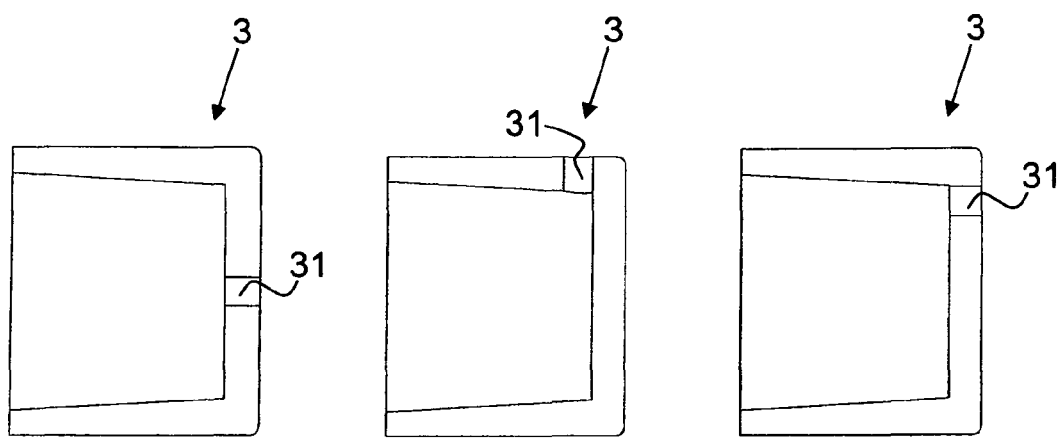
FIG. 9 shows a longitudinal section through a coupling part in a second embodiment.
FIG. 10 shows a longitudinal section through a coupling part in a third embodiment.
FIG. 11 shows a longitudinal section through the coupling part according to FIG. 8.

The port opening 31 may be provided at different locations. In FIG. 8, the port opening 31 is arranged in the upper region in the rear wall of the coupling part 3. In FIG. 9, the port opening 31 is arranged centrally in the rear wall. In FIG. 10, the port opening 31 is arranged in the casing, but in the rear region close to the rear wall, and is preferably arranged in the upper region. FIG. 11 once again shows the situation according to FIG. 8, but without the breast shield 4 plugged in.

If the port opening 31 is arranged at the top, the residual air in the coupling part 3 is sucked off together with the milk and the dead volume is reduced once again. In use, the breast shield 4 and coupling part 3 no longer have any air chambers. The clearances thereof, if still present, are filled with milk. So that the port opening 31 is actually directed upward during use, a corresponding marking 100, for example, can be indicated on the coupling part 3.

Figure 12:
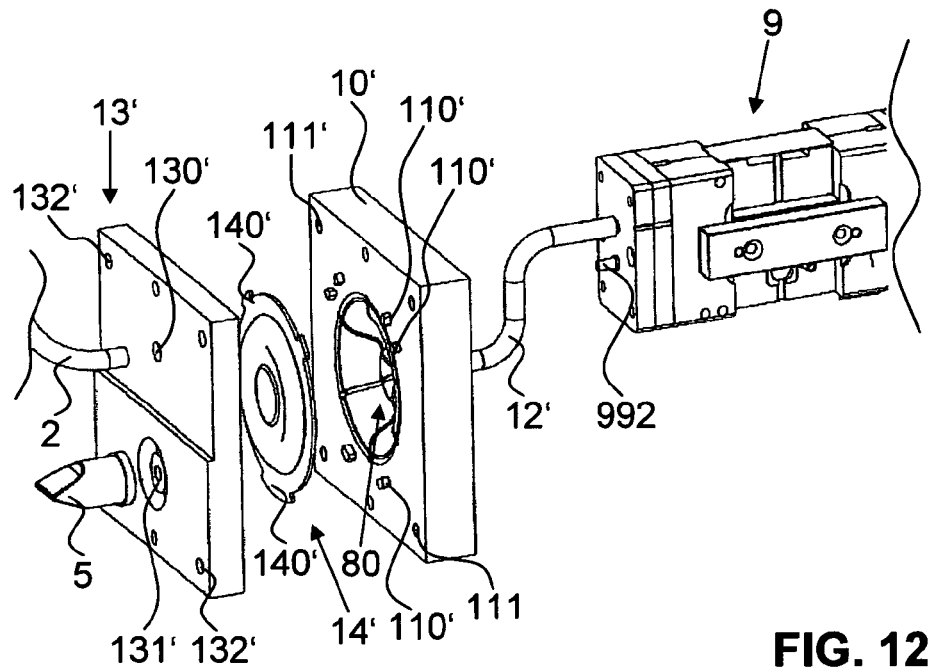
FIG. 12 shows an exploded view of part of the device according to the invention with a pump unit in a third embodiment.
Figure 13:
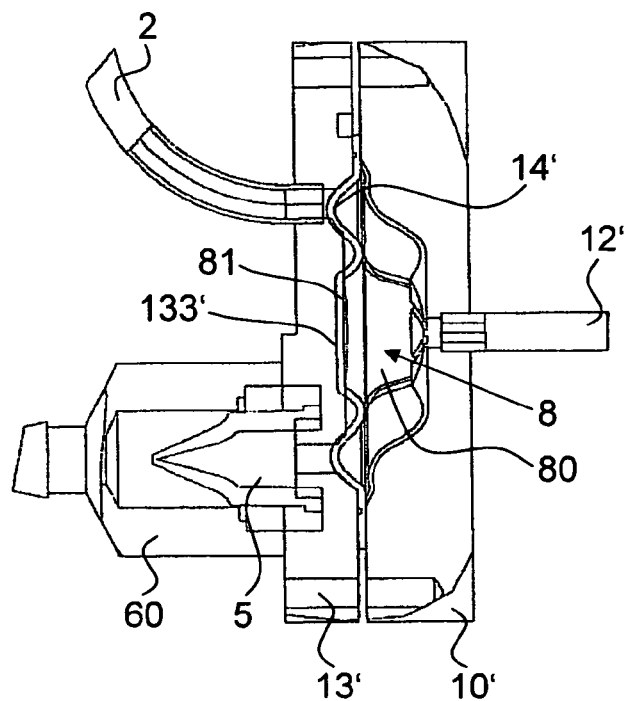
FIG. 13 shows a longitudinal section through part of the device according to FIG. 12.
Figure 14:
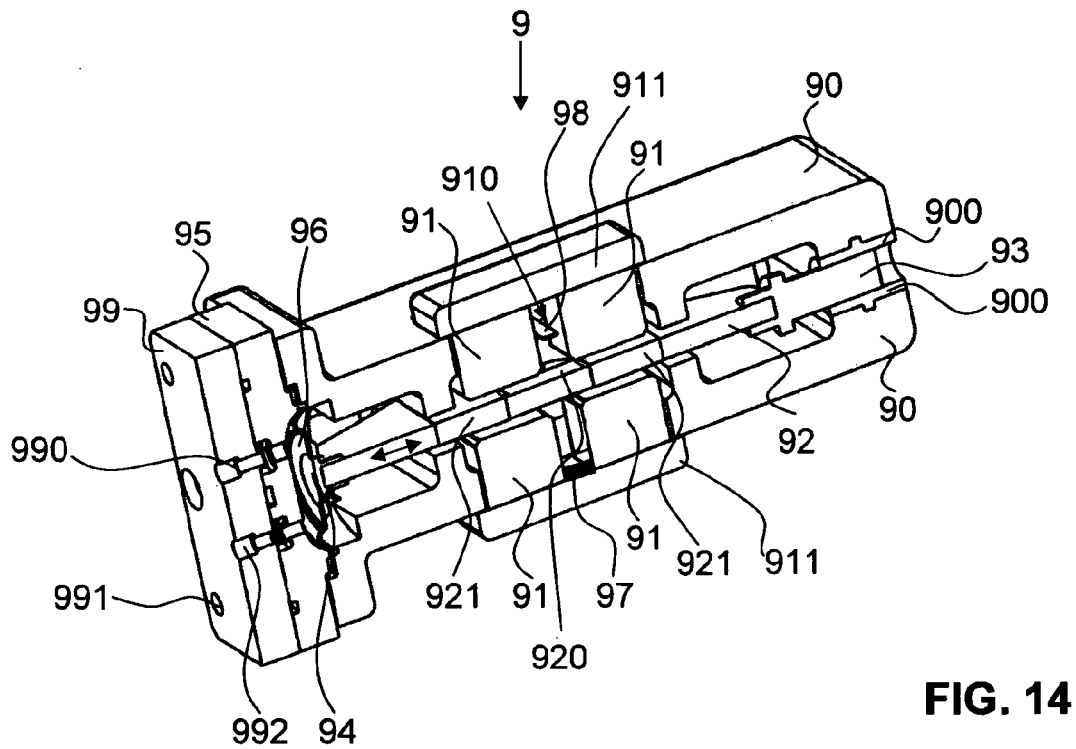
FIG. 14 shows a longitudinal section through the pump unit according to FIG. 12 in a first embodiment.

FIGS. 12 to 14 illustrate an alternative embodiment. The suction line 2 also forms the milk line. The expressed milk is transported on the breast side from the breast shield 4 via the first line to a chamber 8 and from there is transported further into the milk collecting container 7. Furthermore, a diaphragm 14' is also arranged here in the chamber 8, the diaphragm dividing the chamber 8 into a breast-shield-side region and a drive-side or unit-side region.

However, the diaphragm 14' is not the diaphragm of the vacuum pump, as in the previous examples, but an additional diaphragm. As before, the diaphragm 14' has the function of separating media and serves as a partition wall between the breast-shield-side part 81, which is filled with milk during use, and the unit- or pump-side part 80, which has a negative pressure and is filled with air. Furthermore, as before, the diaphragm 14' is moved cyclically, as is described below. As a result, the diaphragm 14' transports the milk from the breast shield 4 through the breast-shieldside part 81 into the milk collecting container 7, irrespective of the relative position of the breast shield 4, the vacuum pump 9, and the milk collecting container 7 with respect to one another. The system also changes here from a pneumatic pump into a hydraulic pump.

The diaphragm 14' illustrated here has a circular outline, the diaphragm having laterally protruding wings 140'. There are three wings 140'. The base plate 10', which in turn may be part of a vacuum pump housing has lateral stops 110' between which the wings 140' are held. As a result, the diaphragm 14' can be held in an unambiguous position in the chamber 8, which facilitates assembly. The wings can also be used in the embodiments described with reference to FIGS. 1 to 11.

The embodiment described here is a separate diaphragm pump, referred to here as a pump unit 9. The diaphragm 14' is connected to the pump unit 9 via a vacuum line 12' and is driven by the pump unit 9 on the basis of the cyclically changing pressure in the vacuum line 12'.

The cover 13' has two ports 130' and 131' for the first and second lines 2, 6 and for the milk collecting container 7, respectively. However, the second port 131' is preferably also provided with a nonreturn valve 5. The connection to the counterplate, which in turn may be part of a pump housing 10, preferably takes place via snap-in or screw connections, wherein the corresponding holes are provided with the designations 132' and 111 in FIG. 12.

The pump unit 9 according to the invention can now be readily seen in FIG. 14. The pump unit 9 has a housing 90, which is preferably manufactured from metal or plastic. The housing 90 preferably has a cuboidal design. A flat iron core 911 and a permanent magnet 91 attached to the flat iron core are arranged on one side of the housing 90. The iron core 911 rests upon the housing 90 such that the permanent magnet 91 is in a recess of the housing. The permanent magnet 91 consists of two parts, which are spaced from one another such that there is a recess 910 between both parts.

There is an identical construction on an opposite side of the housing available again. An iron core 911 and a permanent magnet 91 attached to the iron core are also arranged here.

A flat coil former 92 with a coil 921 wound around the coil former 92 runs between the two mutually opposite pairs of permanent magnets 91. The coil former 92 is of substantially rod-shaped or plate-shaped design. At one end, the coil former is held in a fixed position in a guide bearing 93. The guide bearing 93 is displaceable together with the coil former 92 including the coil 921 relative to the housing 90 and therefore relative to the permanent magnet 91 along the longitudinal axis of the housing 90. For this purpose, the housing 90 has a plain bearing 900. The movement of the coil former 92 is illustrated by a double arrow in FIG. 14.

The other end of the coil former 92 is connected fixedly to a diaphragm, referred to here as the vacuum diaphragm 94. The vacuum diaphragm 94 bears against the housing 90 on the end side thereof and is clamped securely between the housing 90 and a valve plate 95. The diaphragm 94 separates a pump chamber 96 from the coil former 92. The vacuum diaphragm 94 preferably has a circular outline, preferably having a shape customary for diaphragms of diaphragm vacuum pumps. The valve plate 95 is held between the housing 90 and a cover 99. The three parts are preferably connected, for example screwed, tightly to one another in a detachable or nondetachable manner. The corresponding holes are provided with the reference number 991 in the cover 99. The cover 99 has a port opening 990 for the vacuum line 12', which is connected to the pump chamber 96. An air inlet opening 992 in the cover 99 likewise connects the environment to the pump chamber 96 via the valve plate 95. The valve plate 95 has the valves, inlets, and outlets customary for diaphragm vacuum pumps. These are not described in detail here.

If an alternating electric current flows through the coil, the electromagnetic field changes and the coil former 92 moves relative to the permanent magnet 91. The coil former 92 acts like a piston or ram and moves the vacuum diaphragm 94 cyclically to and fro. In this case, the force acting on the vacuum diaphragm 94 is proportional to a current applied to the coil. By means of the movement of the vacuum diaphragm 94, a cyclically changing vacuum is built up in the pump chamber 96. The changes in pressure are passed on via the vacuum line 12' to the chamber 8 where the diaphragm 14' is moved analogously.

The vacuum diaphragm 94 of the pump unit 9 is therefore driven via a linear movement that is generated electromagnetically In comparison to the rotating drives that are otherwise customary, the linear movement of the vacuum diaphragm is quieter. Fewer vibrations and structure-borne sound are generated. In contrast to the prior art, the stroke length can be changed and can be electronically controlled. This permits precise control even under low vacuum levels.

In order for the stroke length to be able to be controlled in a specific manner, the displacement and the position of the coil former 92 is monitored, respectively. Position and/or movement sensors are used for this purpose. In this example, this takes place by means of an optical sensor, which detects a position scale. The position scale 920 is preferably provided on the coil former 92. A light source 97 sends light perpendicularly to the longitudinal direction of the coil former 92 to an opposite detector 98, the light passing through the position scale 920. The coil former is transparent in the region. The light source 97 and the detector 98 are preferably arranged in the recesses 910 of the permanent magnet 91. Other types of position measurement are possible. The measured signal is sent to an electronic controller of the vacuum pump and the current is applied to the coil according to the signal. As a result, the position, the deflection amplitude, and the frequency can be controlled independently of one another. Vacuum values of 0 to 300 mmHg are customarily obtained. The frequencies are customarily 0 to 150 cycles per minute.

As an alternative, instead of the guide bearing 93, there may also be a second diaphragm, which is of similar or identical design to the vacuum diaphragm 94. This results in a symmetrical construction, which likewise ensures guidance and therefore a linear movement of the coil former 92 within the housing 90. In addition, the second diaphragm can likewise be used to build up the vacuum such that the flow rate can be increased.

Figure 15:
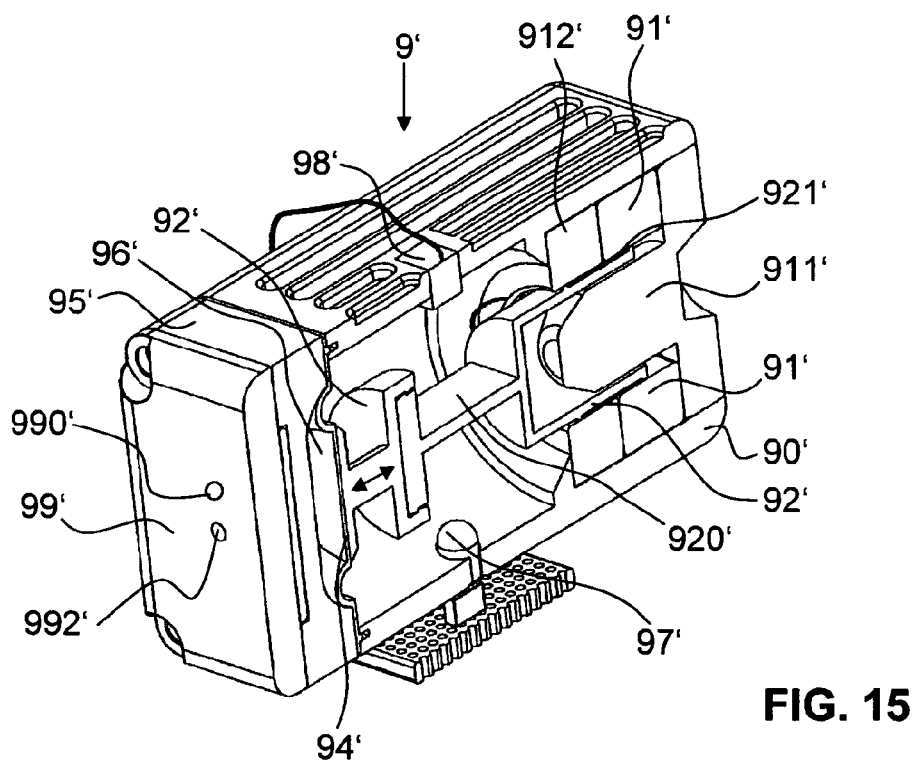
FIG. 15 shows a longitudinal section through a pump unit in a second embodiment.

FIG. 15 shows a further embodiment of a vacuum pump with an electromagnetically generated linear driving movement of the diaphragm. In contrast to the above-described flat coil, a moving coil is used here. The magnet and coil are of annular or cylindrical design, respectively. A housing 90' is also present here. The permanent magnet 91' is held at the rear end of the moving coil remote from the breast shield. The permanent magnet is passed by an iron core 911', which is in contact to the permanent magnet 91' on a first end side thereof. Against the opposite end side of the permanent magnet 91' bears an iron ring 912'. The coil former 92' engages around the iron core 911' and is axially guided by the iron core. The coil former 92' extends between the iron core 911' and the permanent magnet 91' or the iron ring 912'. The coil former is guided without contact in the permanent magnet 91' and in the iron ring 912', respectively. The wound coil 921' surrounds the coil former 92' in this region.

The coil former 92' is also fixedly connected to the vacuum diaphragm 94' and acts as a piston for the linear drive of the vacuum diaphragm 94'. The pump chamber is provided with the reference number 96', the valve plate with the reference number 95' and the cover with the reference number 99'. The port opening has the reference number 990' and the air inlet opening has the reference number 992'. Also here, there is again a position sensor, which indicates the position of the coil former 92' relative to the magnet 91', and therefore the movement and position of the vacuum diaphragm 94', respectively, to a controller in order to control the vacuum. The light source is denoted by the reference number 97', the detector by 98', and the position scale by 920'. The position scale is preferably of a transparent design. In contrast to the previous example, the sensor here is arranged outside the region of the permanent magnet 91'.

The two vacuum pumps described with reference to FIGS. 12 to 15 can also be used in known breast pumps. That is to say, for example, in systems in which the suction line between the vacuum pump and breast shield is separate from the flow of milk.

The elements of the above-described embodiments can be combined with one another individually or in groups in order to form further embodiments.

The invention claimed is:

1. A device for expressing human breast milk, wherein the device has a breast shield for bearing against a mother's breast, and a vacuum pump for generating a vacuum, wherein the device further comprises a line which connects the vacuum pump to the breast shield and is intended for transmitting the vacuum generated to the breast shield, and wherein the device comprises a chamber with a breast-shield side and a pump side, the chamber having a first port on the breast shield side, the line starting at the breast-shield and ending in said first port of said chamber, thereby connecting the breast-shield side of the chamber to the breast shield, wherein the chamber has a second port on the breast-shield side for connection to a milk collecting container, wherein the two ports in the chamber are connected to each other in terms of fluid communication, wherein, during an expressing operation, the line forms a milk line for transporting breast milk expressed in the breast shield to the chamber, and from the chamber to the milk collecting container, wherein the chamber comprises a diaphragm dividing the chamber into the breast-shield side and the pump side, wherein the diaphragm is driven from the pump side only and is designed for conveying the expressed milk, and wherein a drive of the diaphragm serves to generate the vacuum in the chamber and to convey the flow of milk, the device changing during use from an initial pneumatic pumping system to a hydraulic pumping system using said line in the hydraulic pumping system, wherein the expressed milk acts in said line as a working fluid in order to express further milk from the mother's breast, and wherein the second port is provided with a nonreturn valve, which prevents the expressed milk from flowing back from the milk collecting container to the chamber, wherein the breast shield and the chamber remain in fluid communication throughout the duration of the expressing operation.

2. The device as claimed in claim 1, wherein the diaphragm has a substantially circular outline.

3. The device as claimed in claim 1, wherein the diaphragm is driven in the central region thereof.

4. The device as claimed in claim 1, wherein the breast shield has a tubular connector and a funnel, which is integrally formed thereon and is intended for resting on a mother's breast, wherein the funnel widens toward the free side thereof that faces away from the connector, and wherein there is a passage, which extends continuously from a breast-side end of the funnel as far as a pump-side end, being opposite said breast-side end, of the connector and which serves to apply a vacuum to the mother's breast and for the flowing away of the expressed breast milk, wherein the funnel is of more flexible design than the connector, wherein the funnel has a main region extending over a substantial part of the length thereof with a first opening angle of the passage, and a breast-side end region with a second opening angle of the passage, and wherein, when not in use, the first opening angle is smaller than the second opening angle, and wherein, in use, at least the first opening angle can be enlarged by axial pressure on the breast shield.

5. The device as claimed in claim 1, wherein the breast shield has a tubular connecter and a funnel that is integrally formed thereon and is intended for resting against a mother's breast, wherein the funnel has a breast-side diameter of 5 mm to 40 mm and a length of 10 mm to 40 mm, such that, in use, the nipple, and at maximum the areola, is surrounded by the breast shield.

6. The device as claimed in claim 1, wherein the breast shield is arranged in a coupling part, the coupling part having a marking defining an upper side with an upper region, wherein the upper region has a port for the connection of the line.

7. The device as claimed in claim 1, wherein the diaphragm is driven in the center thereof.

8. A coupling part for use in the device according to claim 1, wherein the coupling part connects the breast shield with the line, wherein the line connects the breast shield with a vacuum pump and wherein the line forms a milk line for transporting expressed breast milk, wherein the coupling part comprises a port for connection of the line.

9. The device as claimed in claim 1, wherein the line is a flexible line.

* * * * *